United States Patent [19]

Ueoka et al.

[11] 4,166,191

[45] Aug. 28, 1979

[54] PROCESS FOR PRODUCING HIGHLY PURE P-TERTIARY-BUTYL PHENOL

[75] Inventors: Masakazu Ueoka, Ichikawa; Yasuyuki Iguchi, Ichihara; Takayuki Saito, Hitachi; Hiroshi Okamura, Chiba, all of Japan

[73] Assignees: Hitachi Chemical Company, Ltd.; Maruzen Oil Co, Ltd.; Goi Chemical Co, Ltd., all of Japan

[21] Appl. No.: 876,318

[22] Filed: Feb. 9, 1978

Related U.S. Application Data

[63] Continuation of Ser. No. 729,795, Oct. 5, 1976, abandoned.

[30] Foreign Application Priority Data

Sep. 20, 1976 [JP] Japan ................................ 51-112804

[51] Int. Cl.$^2$ ............................................. C07C 39/06

[52] U.S. Cl. .................................................... 568/789
[58] Field of Search .......................................... 568/789

[56] References Cited

U.S. PATENT DOCUMENTS 2,578,597  12/1951  Robinson ............................. 568/789
3,876,710  12/1975  Saito et al. ........................... 568/789

*Primary Examiner*—Werren B. Lone
*Attorney, Agent, or Firm*—Craig and Antonelli

[57] ABSTRACT

Highly pure p-tertiary-butyl phenol can be prepared from an olefin composition comprising a major amount of at least one isobutylene oligomer and a minor amount of a codimer of n-butene and isobutylene. The reaction of said olefin composition with phenol is carried out in the presence of water and synthetic silica-alumina catalyst at a temperature of 140°–230° C.

20 Claims, No Drawings

PROCESS FOR PRODUCING HIGHLY PURE P-TERTIARY-BUTYL PHENOL

This is a continuation of application Ser. No. 729,795, filed Oct. 5, 1976, now abandoned.

This invention relates to an improved process for producing highly pure p-tertiary-butyl phenol, hereinafter referred to as PTBP.

Heretofore, there has been proposed a process for producing PTBP which comprises using isobutylene and phenol as starting materials, carrying out alkylation reaction using such a catalyst as sulfuric acid, aluminum chloride, or the like, and isomerizing the resulting product mixture in another isomerization step at a high temperature. Since said process aims at producing only PTBP and there are contained a large amount of by-products other than PTBP, it is necessary to convert these by-products to the desired PTBP by isomerization at a high temperature. Consequently, said process inevitably requires two steps for the reaction, which are complicated and industrially very disadvantageous.

There has also been proposed a process for producing PTBP using diisobutylene and phenol as starting materials and such a solid acid catalyst as synthetic zeolite. According to said process, if impurities such as a codimer of n-butene and isobutylene (hereinafter referred to as COD) are included in the starting diisobutylene, there are produced ortho-secondary-butyl phenol (hereinafter referred to as OSBP), para-secondary-butyl phenol (hereinafter referred to as PSBP), and the like together with the desired PTBP. Since it is impossible to rearrange OSBP and PSBP to PTBP and the boiling points of OSBP and PSBP are very close, it is remarkably difficult to isolate OSBP and PSBP each other using such a method as rectification. This results in decreasing purity of PTBP in the product.

PTBP is an important compound as a starting material for producing plasticizers, resins, spices, polymerization inhibitors, antioxidants, molecular weight regulators, and the like. If impurities are included in PTBP, they decrease not only commercial value of PTBP by causing coloring and coagulation with the lapse of time but also properties and purity of the final products.

Therefore, if diisobutylene contains as an impurity a codimer of n-butene and isobutylene (COD) and the former is used as the starting material, it is necessary to prevent the production of OSBP and PSBP.

Isobutylene oligomers produced industrially contain COD, the amount of which depends on their production methods. Further it is difficult to remove COD from isobutylene oligomers by distillation, since specific volatility of isobutylene oligomers and COD is small. Heretofore, there has been no proposal for producing PTBP using as a starting material isobutylene oligomers containing COD. The present inventors have studied a way to solve the problems mentioned above caused by using isobutylene oligomers containing COD and accomplished the present invention.

It is an object of the present invention to remove disadvantages caused by COD. It is another object of the present invention to provide a process for producing highly pure PTBP in high yield without or hardly by-producing OSBP and PSBP by using isobutylene oligomers containing COD as an impurity as a starting material.

In accordance with the present invention, highly pure p-tertiary-butyl phenol (PTBP) is produced by using as a starting material an olefin composition comprising a major amount of at least one isobutylene oligomer and a minor amount of a codimer of n-butene and isobutylene (COD), reacting said olefin composition with phenol in the presence of water and synthetic silica-alumina catalyst at a temperature of 140°–230° C. to carry out selective reaction of said isobutylene oligomer.

The olefin composition comprises a major amount of at least one isobutylene oligomer and a minor amount of COD. As the isobutylene oligomers, at least one member selected from the group consisting of dimer to pentamer of isobutylene is preferably used. The proportion of COD in the olefin composition is usually 0.5 to 30% by weight.

The reaction of the olefin composition with phenol is carried out in the liquid state, usually under pressure, in the presence or absence of a solvent using a synthetic silica-alumina catalyst under solid-liquid contact conditions.

The reaction temperature used is from 140° to 230° C. If the reaction temperature is below 140° C., the the reaction rate unfavorably decreases and if above 230° C., OSBP and PSBP are unfavorably by-produced easily.

The presence of water in the reaction system is necessary to suppress the by-production of OSBP and PSBP. The amount of water used is usually 0.01 to 5% by weight, preferably 0.05 to 3% by weight, in the reaction solution.

The synthetic silica-alumina catalyst contains 10–40% by weight, preferably 15–35% by weight of alumina ($Al_2O_3$) and 60–90% by weight, preferably 65–85% by weight of silica ($SiO_2$) as main components, and may further contain metal oxides of metals of the group II, III and IVb of the periodic table. Synthetic silica-alumina catalysts containing 10–40% by weight of alumina and 60–90% by weight of silica have not only higher catalytic activity and physical strengths, but also longer catalyst life. Synthetic silica-alumina catalysts containing silica and alumina outside the above-mentioned ranges are not preferable because their catalytic activities are low. The catalysts used in the present invention are calcined at 500°–800° C., preferably 550°–750° C. for 0.5 to 5 hours, preferably 1 to 3 hours. If the calcination temperature is outside the above-mentioned range, catalytic activity decreases.

In the present reaction, it is preferable to use 1 to 5 moles of phenol per mole of isobutylene oligomer in terms of isobutylene. The use of an excessively large amount of phenol is not preferable, since larger capacity of the reaction apparatus is required and utility costs increase. On the other hand, the use of too small amount of phenol is not preferable, since disproportionation, polymerization, and the like of isobutylene oligomer take place.

In the reaction system, there may be present compounds which can be isomerized or converted to PTBP. For example, ortho-tertiary-butyl phenol, di-tertiary-butyl phenol, para-octyl phenol, etc. which are by-produced together with PTBP can be recycled to the reaction system to be isomerized or converted to PTBP, or there may be present in the reaction system compounds which can be isomerized or converted to PTBP produced by another process.

Any pressure is applicable to the reaction system, so long as the reactants and the solvent, if used, can be kept in the liquid state at a reaction temperature under the application of pressure.

A solvent may be used, if required. Any solvents which can dissolve the reactants and be chemically inert to the reactants and the catalyst, e.g. straight-chain or alicyclic saturated hydrocarbons such as pentane, hexane, cyclopentane, cyclohexane, may be used.

The reaction can be carried out by either batch or flow system. If a flow system is used, preferable contact time between the starting materials and the catalyst is 0.2 to 4 liter of catalyst/(l./hr) of feed. If the contact time is too short, selectivity for PTBP lowers and if too long, OSBP and PSBP are unfavorably by-produced easily.

The present invention is illustrated by the following examples in which percents are given as percents by weight.

EXAMPLES 1 TO 3

A flow system reactor having an inner diameter of ¾ inch was used. Each catalyst having silica and alumina contents as shown in Table 1 calcined at 700° C. and molded into a cylindrical form having a diameter of 3 mm was placed in the reactor. An olefin composition as shown in Table 1 and phenol, the molar ratio of phenol to isobutylene oligomer (in terms of isobutylene) being 1.5, were fed to the reactor at a contact time of 1.2 liter of catalyst/(l/hr) of feed and each reaction was carried out under a pressure of 10 kg/cm$^2$ (gauge) and other conditions as set forth in Table 1.

The results are as set forth in Table 1. In Table 1, products were analyzed by using gas chromatography; water concentration is shown in percent in the reaction solution; DIB and TIB in an olefin composition mean diisobutylene and triisobutylene, respectively.

COMPARATIVE EXAMPLE 1

The process of Example 1 was repeated except for changing the reaction temperature to 240° C. and the water concentration in the reaction solution to 0.8%. The results are set forth in Table 1.

COMPARATIVE EXAMPLE 2

The process of Example 2 was repeated except for using synthetic zeolite as a catalyst. The synthetic zeolite was prepared as follows. 2014 Grams of chlorides of rare earth metals were dissolved in 16,510 cc of ion exchange water and 2000 g of crystalline synthetic faujasite (dry base) was mixed with the resulting solution to carry out ion exchange. The mixture was filtered under suction and washed with ion exchange water. After dehydrating, the resulting faujasite was dried at 110° C. for 16 hours and calcined in a muffle furnace at 550° C. for 3 hours. Degree of ion exchange with rare earth metals was 68.0% by mole. The same procedure of ion exchange was repeated and the resulting faujasite was dried at 110° C. for 16 hours after water washing. Degree of ion exchange with rare earth metals was 90.3% by mole. The thus obtained faujasite (850 g) was mixed with 180 g of Japanese acid clay and molded into cylinders having the diameter of 3 mm. The cylinders were calcined at 110° C. for 16 hours and further at 500° C. for 2 hours and made all of suitable uniform length. The resulting catalyst had apparent bulk density of 0.51 g/cc and pressure resistence of 2.8 kg.

The results obtained are set forth in Table 1.

COMPARATIVE EXAMPLE 3

The process of Example 3 was repeated except for using synthetic zeolite. The results are set forth in Table 1.

COMPARATIVE EXAMPLE 4

The process of Example 2 was repeated except for changing the water concentration in the reaction solution to 0%. The results are set forth in Table 1.

As is clear from Table 1, according to the present process, no or almost no OSBP and PSBP, which are impossible to be converted to PTBP, are produced and PTBP can be obtained in high yield. In Example 1, no OSBP nor PSBP is produced but para-octyl phenol is produced in 34.6% yield and the yield of PTBP is not so high. But para-octyl phenol can easily be dealkylated to PTBP with heating, PTBP can be obtained in high yield as a result.

As mentioned above, according to the process of the present invention, PTBP can be obtained in high yield and no or almost no OSBP and PSBP, which are impossible to be converted to PTBP, are produced, so that highly pure PTBP can be produced even though COD is present as an impurity in the starting isobutylene oligomers.

Table 1

| | | Example | | | Comparative Example | | | |
|---|---|---|---|---|---|---|---|---|
| | | 1 | 2 | 3 | 1 | 2 | 3 | 4 |
| Olefin | DIB | 94 | 94 | 43 | 94 | 94 | 43 | 94 |
| composition | TIB | — | — | 35 | — | — | 35 | — |
| (%) | COD | 6 | 6 | 22 | 6 | 6 | 22 | 6 |
| Water concentration (%) | | 0.5 | 0.8 | 0.8 | 0.8 | 0.8 | 0.8 | 0 |
| Catalyst Al$_2$O$_3$ (%) | | 27 | 15 | 27 | 27 | *1 | *1 | 15 |
| SiO$_2$ (%) | | 73 | 85 | 73 | 73 | | | 85 |
| Reaction temp. (°C.) | | 160 | 200 | 200 | 240 | 200 | 200 | 200 |
| Reaction products composition (%) | | | | | | | | |
| PTBP | | 55.20 | 80.50 | 79.31 | 84.98 | 83.15 | 75.30 | 82.50 |
| o-Tert-Bu Ph | | 5.13 | 3.67 | 3.50 | 2.13 | 2.23 | 3.51 | 2.01 |
| m-Tert-Bu Ph | | 0.23 | 0.51 | 0.60 | 2.10 | 0.98 | 0.90 | 2.98 |
| 2,4-Di-tert-Bu Ph | | 4.84 | 10.10 | 9.93 | 7.20 | 7.31 | 9.53 | 7.10 |
| p-Octyl Ph | | 34.60 | 5.19 | 6.59 | 2.29 | 4.46 | 3.35 | 3.86 |
| OSBP | | 0.00 | 0.02 | 0.05 | 1.05 | 1.54 | 6.51 | 1.25 |
| PSBP | | 0.00 | 0.01 | 0.02 | 0.25 | 0.33 | 0.90 | 0.30 |
| CSBP/PTBP × 100 (%) | | 0.00 | 0.03 | 0.06 | 1.24 | 1.85 | 8.65 | 1.52 |
| PSBP/PTBP × 100 (%) | | 0.00 | 0.01 | 0.03 | 0.29 | 0.40 | 1.20 | 0.36 |

Note)
*1: Synthetic zeolite. Bu = butyl, Ph = phenol

EXAMPLE 4

In a 200 cc autoclave, 28.5 g of an olefin composition containing 94% of diisobutylene and 6% of COD, 71.5 g of phenol, 0.8 g of water and 10 g of a silica-alumina catalyst containing 27% of Al$_2$O$_3$ and 73% of SiO$_2$ calcined at 700° C. were placed. The reaction was carried out at 200° C. for 2 hours under 8 kg/cm$^2$ of N$_2$ gas. The reaction products obtained were analyzed by gas chromatography. The results are as follows:

| | |
|---|---|
| PTBP | 78.30 (%) |
| o-Tert-butyl phenol | 4.13 |
| m-Tert-butyl phenol | 0.45 |
| 2,4-Di-tert-butyl phenol | 10.21 |
| p-Octyl phenol | 7.33 |
| OSBP | 0.02 |
| PSBP | 0.01 |
| OSBP/PTBP × 100 | 0.03 |

-continued

| | |
|---|---|
| PSBP/PTBP × 100 | 0.01 |

What is claimed is:

1. A process for producing highly pure p-tertiary-butyl phenol which comprises using as a starting material an olefin composition comprising a major amount of at least one isobutylene oligomer and 0.5–30% by weight of a codimer of n-butene and isobutylene, reacting said olefin composition with phenol in the presence of sufficient water 0.5–5% by weight to suppress the by-production of ortho-secondary-butyl phenol and para-secondary-butyl phenol and in the presence of a synthetic silica-alumina catalyst at a temperature of 140°–230° C. to selectively react said isobutylene oligomer, whereby a highly pure p-tertiary-butyl phenol can be formed using said olefin composition as a starting material.

2. A process according to claim 1, wherein the synthetic silica-alumina catalyst comprises 10–40% by weight of alumina and 90–60% by weight of silica.

3. A process according to claim 1, wherein the synthetic silica-alumina catalyst comprises 15–35% by weight of alumina and 85–65% by weight of silica.

4. A process according to claim 1, wherein the synthetic silica-alumina catalyst is calcined at 500°–800° C.

5. A process according to claim 1, wherein the isobutylene oligomer is at least one member of dimer to pentamer of isobutylene.

6. A process according to claim 1, wherein 1–5 moles of phenol is used per mole of isobutylene oligomer in terms of isobutylene.

7. A process according to claim 1, wherein 0.01–5% by weight of water is present in the reaction solution.

8. A process according to claim 1, wherein 0.05–3% by weight of water is present.

9. A process according to claim 1, wherein an olefin composition comprising 70–99.5% by weight of at least one isobutylene oligomer selected from dimer to pentamer of isobutylene and 30–0.5% by weight of a codimer of n-butene and isobutylene is reacted with phenol, 1–5 moles of phenol being used per mole of isobutylene oligomer in terms of isobutylene, in the presence of 0.05–3% by weight of water and a synthetic silica-alumina catalyst comprising 15–35% by weight of alumina and 85–65% by weight of silica, calcined at 500°–800° C., at a temperature of 140°–230° C. to selectively react the isobutylene oligomer.

10. A process according to claim 1, wherein the reaction of said olefin composition with phenol is carried out in the liquid state under pressure.

11. A process according to claim 1, wherein the synthetic silica-alumina catalyst further contains at least one oxide of a metal of the group II, III or IVb of the Periodic Table.

12. A process according to claim 1, wherein a solvent is present, said solvent being capable of dissolving said starting material and being chemically inert to said starting material and said catalyst.

13. A process according to claim 12, wherein said solvent is a straight chain or alicyclic saturated hydrocarbon.

14. A process according to claim 1, wherein the reaction is carried out by a flow system.

15. A process according to claim 14, wherein the reaction is carried out by the flow system and the contact time between the starting material and the catalyst is 0.2 to 4 liter of catalyst/(l/hr) of feed.

16. A process according to claim 4, wherein the synthetic silica-alumina catalyst is calcined at 550°–750° C.

17. A process according to claim 4, wherein the synthetic silica-alumina catalyst is calcined for a period of 0.5 to 5 hours.

18. A process according to claim 17, wherein the period is 1 to 3 hours.

19. A process according to claim 9, wherein the reaction of said olefin composition with phenol is carried out in the liquid state under pressure.

20. A process for producing highly pure p-tertiary-butyl phenol which comprises reacting an olefin composition consisting essentially of 70–99.5% by weight of at least one isobutylene oligomer selected from the group consisting of a dimer, trimer, tetramer and pentamer of isobutylene and 30–0.5% by weight of a codimer of n-butene and isobutylene with phenol, 1–5 moles of phenol being used per mole of said isobutylene oligomer in terms of isobutylene, in the presence of 0.05–3% by weight of water to suppress the by-production of ortho-secondary-butyl phenol and para-secondary-butyl phenol and in the presence of a synthetic silica-alumina catalyst, calcined at 500°–800° C., comprising 15–35% by weight of alumina and 85–65% by weight of silica at a temperature of 140°–230° C. to selectively react said isobutylene oligomer, whereby a highly pure p-tertiary-butyl phenol can be formed using said olefin composition as a reactant.

* * * * *